United States Patent
Mukaiyama et al.

(10) Patent No.: US 6,222,072 B1
(45) Date of Patent: Apr. 24, 2001

(54) PROCESS FOR PRODUCING OPTICALLY ACTIVE AMINE

(75) Inventors: Teruaki Mukaiyama, Tokyo; Kiyoaki Sugi; Takushi Nagata, both of Yamaguchi; Toru Yamada, Tokyo, all of (JP)

(73) Assignee: Mitsui Chemicals Inc., Tokyo (JP)

( * ) Notice: Subject to any disclaimer, the term of this patent is extended or adjusted under 35 U.S.C. 154(b) by 0 days.

(21) Appl. No.: 09/186,626

(22) Filed: Nov. 6, 1998

Related U.S. Application Data

(63) Continuation-in-part of application No. PCT/JP98/00938, filed on Mar. 6, 1998.

(30) Foreign Application Priority Data

Mar. 6, 1997 (JP) .................................................. 9-052061

(51) Int. Cl.$^7$ .................................................. C07B 57/00
(52) U.S. Cl. ......................... 564/304; 546/150; 549/404; 564/12; 564/92
(58) Field of Search ............................... 564/12, 92, 304; 546/150; 549/404

(56) References Cited

PUBLICATIONS

Chem Abstracts 1997:132177, Hashiguchi et al.*
C.P. Chen et al., Tetrahedron Lett., (1991), 32, pp. 7175–1778.

A.S. Thompson et al., J. Org. Chem., 58, (1993), pp. 5886–5888.

Shohei Hashiguchi et al., Journal of Association of Organic Synthetic Chemistry 55, (1997), pp. 99–109.

Y. Nishida et al., Inorg. Chim. Acta., 38, (1980), pp. 213–219.

E.G. Jager, Z. Chem., 8, (1968), pp. 30, 392–393 and 470–471.

* cited by examiner

*Primary Examiner*—Samuel Barts
(74) *Attorney, Agent, or Firm*—Birch, Stewart, Kolasch & Birch, LLP

(57) ABSTRACT

A novel process for producing an optically active amine is provided. The optically active amine is adapted for use as an intermediate in synthesizing physiologically active compounds such as pharmaceuticals and agricultural chemicals, as a functional material such as a liquid crystal, and as a starting material in synthesizing fine chemicals. The process comprises the step of reacting an imine with a hydride reagent in the presence of an optically active metal compound and an alcohol compound and/or carboxylic acid compound.

11 Claims, No Drawings

PROCESS FOR PRODUCING OPTICALLY ACTIVE AMINE

This application is a Continuation-In-Part of PCT application no. PCT/JP98/00938 filed on Mar. 6, 1998, which designated the United States and on which priority is claimed under 35 U.S.C. §120, the entire contents of which are hereby incorporated by reference.

TECHNICAL FIELD

This invention relates to a process for producing an optically active amine. More specifically, this invention relates to a process for producing an optically active amine which is adapted for use as an intermediate in synthesizing physiologically active compounds such as pharmaceuticals and agricultural chemicals, as a functional material such as a liquid crystal, and as a starting material in synthesizing fine chemicals.

BACKGROUND TECHNOLOGY

A common process for producing an optically active amine is the process wherein a nitrogen functional group is introduced in an optically active alcohol by substitution reaction (See, for example, C. P. Chen et al., Tetrahedron Lett., 32, 7175 (1991); A. S. Thompson et al., J. Org. Chem. 58, 5886 (1993), etc) This process, however, is associated with a safety problem due to the use of an azide compound which suffer from the risk of explosion, and as a consequence, the control of the production process was complicated.

In view of such situation, various production processes have been proposed wherein an optically active amine compound is directly produced from the corresponding imine by an asymmetric reducing reaction. (For a general review, see, for example, Shohei HASHIGUCHI et al., Journal of Synthetic Organic Chemistry Japan, 55, 99 (1997)). A known process is the process wherein an imine is asymmetrically hydrogenated by using a rhodium, iridium or titanium complex having a chiral ligand. This process, however, required use of hydrogen atmosphere at a pressure as high as 40 to 130 atm., and the preparation of the catalyst was quite complicated.

Another process is the hydride reducing process wherein an imine is reduced by using an optically active metal hydride comprising a metal hydride complex compound such as lithium aluminum hydride or sodium borohydride or a metal hydride such as diborane modified with an optically active protonic compound. Exemplary such process is asymmetric hydride reduction process using an optically active hydride modified with an optically active alcohol, amine, or amino alcohol. This process, however, requires the use of an equivalent amount of the optically active compound.

In view of such situation, many investigations have been conducted to develop a hydride reducing process wherein the asymmetry source of only catalytic amount is required. For example, in a process using oxazaborolidine complex, an asymmetric reducing reaction using a catalytic amount of the oxazaborolidine complex is realized as in the case of the asymmetric reducing reaction of a ketone. However, when the amount of the asymmetricity source, namely, the complex is reduced from the equivalent amount to the catalytic amount in this process, the resulting product suffers from significantly reduced optical purity. In addition, use of the borane-sulfide complex for the reducing agent also resulted in the complexity of the process, requiring countermeasures for safety, odor, and the like.

SUMMARY OF THE INVENTION

In view of such situation, an object of the present invention is to provide a novel process for producing an optically active amine which is adapted for use as an intermediate in synthesizing physiologically active compounds such as pharmaceuticals and agricultural chemicals, as a functional material such as a liquid crystal, and as a starting material in synthesizing fine chemicals, and such an optically active amine is produced by using a hydride reducing agent which is convenient to handle, and at a high catalytic efficiency through use of a catalytic amount of a chiral auxiliary.

To solve such situation, the inventors of the present invention have made an intensive study on the production of the optically active amine from an imine by using hydride reducing agents with good handling convenience. As a result of such study, the inventors found that the object as described above can be accomplished by the reaction using an optically active metal compound for the catalyst.

In order to solve the situation as described above, there is provided according to the present invention a process for producing an optically active amine comprising the step of reacting an imine with a hydride reagent in the presence of an optically active metal compound.

The present invention also provides a process for producing an optically active amine comprising the step of reacting an imine with a hydride reagent in the presence of an optically active metal compound and an alcohol compound.

The present invention also provides a process for producing an optically active amine comprising the step of reacting an imine with a hydride reagent in the presence of an optically active metal compound and a carboxylic acid compound.

The present invention also provides a process for producing an optically active amine comprising the step of reacting an imine with a hydride reagent in the presence of an optically active metal compound, an alcohol compound and a carboxylic acid compound.

In the process of the present invention, the optically active metal compound used for the catalyst is preferably an optically active cobalt (II) complex.

In the process of the present invention, it is particularly preferable that the optically active cobalt (II) complex comprises a compound represented by the following general formula (a):

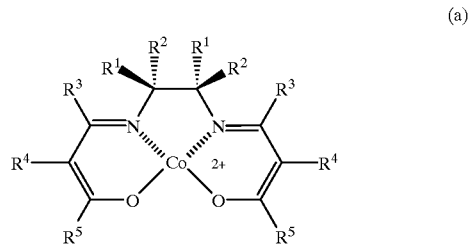

(a)

wherein $R^1$ and $R^2$ are different from each other, and are independently hydrogen atom, a straight chain or branched alkyl group or an aryl group which may be optionally substituted with a substituent; and $R^1$ and $R^1$ or $R^2$ and $R^2$ may together form a ring; and $R^3$, $R^4$ and $R^5$ are the same or different from each other, and are independently hydrogen atom, a straight chain or branched alkyl group, an aryl group, an acyl group, or an alkoxycarbonyl group which may be optionally substituted with a substituent; and $R^4$, $R^5$, and the carbon atoms having $R^4$ and $R^5$ bonded thereto may together form a ring.

BEST MODE FOR CARRYING OUT THE INVENTION

Next the process for producing an optically active amine according to the present invention (hereinafter referred to as "the process of the present invention") is described in detail.

It should be noted that the language "a process . . . comprising the step of reacting an imine with a hydride reagent in the presence of an optically active metal compound" means either that the process consists of the step of reacting an imine with a hydride reagent in the presence of an optically active metal compound, or that the process comprises such step and one or more other steps.

In the process of the present invention, the imine used for the starting material is not limited to any particular type as long as the imine used is a prochiral compound which has a carbon-nitrogen double bond, and the imine used may be adequately selected in accordance with the desired optically active amine.

The process of the present invention is particularly suitable for producing the optically active amine by using the imine represented by the following general formula (b):

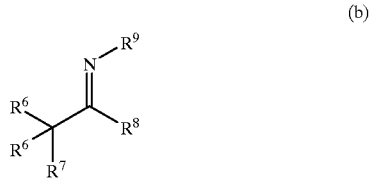

(b)

for the starting material to thereby produce the corresponding optically active amine.

In the formula (b), $R^6$, $R^7$, $R^8$ and $R^9$ may be the same or different from each other, and may be hydrogen atom, a halogen atom, nitro group, nitroso group, cyano group, an alkoxy group, an aryloxy group, silyl group, an alkoxycarbonyl group, thiocarbonyl group, an alkoxythiocarbonyl group, an amino group, an amine oxide group, a hydrazine group, a hydrazone group, an acylhydrazone group, a sulfide group, a sulfinyl group, a sulfonyl group, a phosphino group, a phosphinyl group, a phosphorus group, an acyl group, a straight chain or branched alkyl group, a cycloalkyl group, an alkenyl group, an alkynyl group, or an aryl group, which may be optionally substituted with a substituent. Typical halogen atoms for the $R^6$, $R^7$, $R^8$ and $R^9$ include fluorine, chlorine and bromine; and typical alkoxy groups include methoxy group, ethoxy group, and benzyloxy group. Typical aryloxy groups include phenoxy group, and typical alkoxycarbonyl groups include methoxycarbonyl group, ethoxycarbonyl group, n-butoxycarbonyl group, n-octyloxycarbonyl group, and benzyloxycarbonyl group. Typical alkoxythiocarbonyl groups include methoxythiocarbonyl group, ethoxythiocarbonyl group, n-butoxythiocarbonyl group, n-octyloxythiocarbonyl group, and benzyloxythiocarbonyl group, and typical acyl groups include acetyl group and propionyl group. Typical straight chain or branched alkyl groups include methyl group, ethyl group, n-propyl group, and n-butyl group, and typical cycloalkyl groups include cyclohexyl group. Typical aryl groups include phenyl group, p-methoxyphenyl group, p-chlorophenyl group, p-fluorophenyl group, α-naphthyl group, and β-naphthyl group, and aromatic substituents of heterocyclic rings such as furan ring, thiophene ring and pyridine ring. Typical alkenyl groups include 1-propenyl group, 1-butenyl group, 1-cyclohexenyl group, and styryl group, and typical alkynyl groups include 1-propynyl group, 1-butynyl group, phenylethynyl group, and 2-(trimethylsilyl)ethynyl group.

Typical imines which may be used for the starting material in the process of the present invention include N-(α-methylbenzylidene)methylamine, N-(α-methylbenzylidene)benzylamine, N-(α-methylbenzylidene)hydroxylamine, N-(α-methylbenzylidene)methoxyamine, N-(α-methylbenzylidene)benzyloxyamine, N-(α-methylbenzylidene)benzoyloxyamine, N-(α-methylbenzylidene)benzoylaminoamine, 4-methyl-N-(α-methylbenzylidene)benzenesulfonamide, P,P-diphenyl-N-(α-methylbenzylidene)phosphonamide, P,P-diethoxy-N-(α-methylbenzylidene)phosphonamide, P,P-diphenyl-N-[1-(1,2,3,4-tetrahydronaphthylidene)]phosphonamide, P,P-diphenyl-N-(1-cyclohexylethylidene)phosphonamide, and 1-methyl-3,4-dihydroisoquinoline, and the like.

Among these, the process of the present invention is particularly useful for producing an amine by starting from a condensed ring imine which is typically a benzylidene-N-substituted amine represented by the following formula (b-1), a 1-(1,2,3,4-tetrahydronaphthylidene)-N-substituted amine represented by the following formula (b-2), a N-substituted imino-3,4-dihydro-2H-1-benzopyrane represented by the following formula (b-3), or an isoquinoline alkaloid derivative represented by the following formula (b-4):

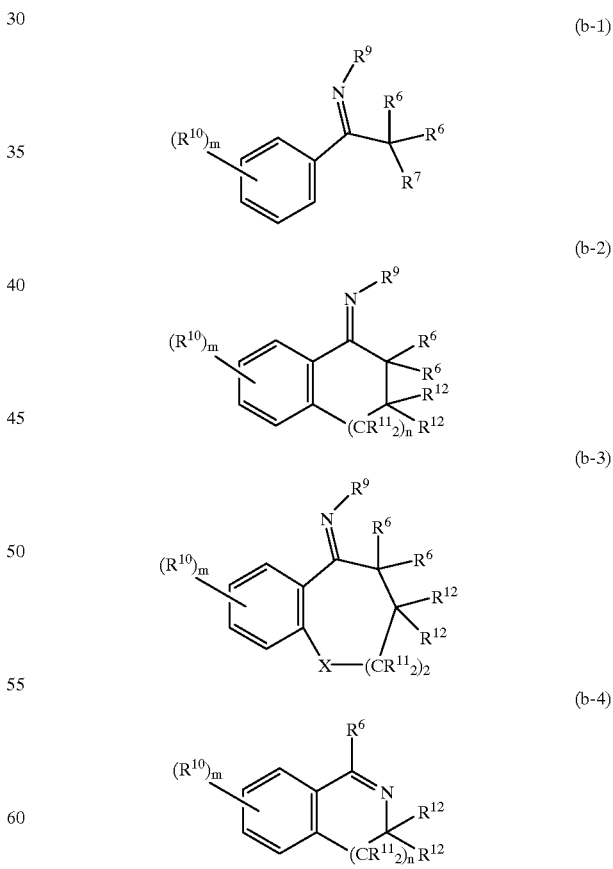

In the formulae (b-1), (b-2), (b-3) and (b-4), $R^6$, $R^7$ and $R^9$ are as defined above for the formula (b). $R^{10}$, $R^{11}$ and $R^{12}$ may be the same or different, and may be hydrogen atom, a halogen atom, nitro group, nitroso group, cyano group, an alkoxy group, an aryloxy group, acyl group, an alkoxycarbonyl group, thiocarbonyl group, an alkoxythiocarbonyl group, an amino group, an amine oxide group, a hydrazine group, a hydrazone group, an acylhydrazone group, a sulfide group, a sulfinyl group, a sulfonyl group, a phosphino group, a phosphinyl group, a phosphorus group, a silyl group, a straight chain or branched alkyl group, a cycloalkyl group, or an aryl group, which may be optionally substituted with a substituent.

Typical halogen atoms for the $R^{10}$, $R^{11}$ and $R^{12}$ include fluorine, chlorine and bromine.

Typical alkoxy groups include methoxy group, ethoxy group, and bezyloxy group, and typical aryloxy groups include phenoxy group. Typical acyl groups include acetyl group and propionyl group, and typical alkoxycarbonyl groups include methoxycarbonyl group, ethoxycarbonyl group, n-butoxycarbonyl group, n-octyloxycarbonyl group, and benzyloxycarbonyl group. Typical alkoxythiocarbonyl groups include methoxythiocarbonyl group, ethoxythiocarbonyl group, n-butoxythiocarbonyl group, n-octyloxythiocarbonyl group, and benzyloxythiocarbonyl group.

Typical amino groups include dimethylamino group and diethylamino group, and typical amine oxide groups include dimethylaminoxide group and diethylaminoxide group. Typical hydrazine groups include methylhydrazine group and ethylhydrazine group, and typical hydrazone groups include methylhydrazone group and ethylhydrazone group. Typical acylhydrazone groups include acetylhydrazone group and propionylhydrazone group.

Typical sulfide groups include methylsulfide group, benzylsulfide group, and phenylsulfide group; typical sulfinyl groups include methyl sulfinyl group and benzyl sulfinyl group, and typical sulfonyl groups include methylsulfonyl group, benzylsulfonyl group, and phenylsulfonyl group.

Typical phosphino groups include dimethylphosphino group, dibenzylphosphino group, and diphenylphosphino group; typical phosphinyl groups include dimethylphosphinyl group, dibenzylphosphinyl group, and diphenylphosphinyl group; and typical phosphorus groups include dimethyl phosphorus group, dibenzylphosphorus group, and diphenylphosphorus group.

Typical silyl groups include trimethylsilyl group, and t-butyldimethylsilyl group.

Typical straight chain or branched alkyl groups for the $R^{10}$, $R^{11}$ and $R^{12}$ include methyl group, ethyl group, isopropyl group, t-butyl group, sec-butyl group, and n-butyl group, and typical cycloalkyl groups include cyclohexyl group. Typical aryl groups include phenyl group, p-methoxyphenyl group, p-chlorophenyl group, p-fluorophenyl group, α-naphthyl group, and β-naphthyl group, and aromatic substituents of heterocyclic rings such as furan ring, thiophene ring and pyridine ring.

n is 0 or an integer, and preferably an integer of 0 to 5; and m is an integer of 1 to 4. When m is an integer of 2 to 4, the plurality of $R^{11}$ may be the same or different. The plurality of $R^6$, $R^{11}$ or $R^{12}$ may together form a ring, and for example, they may together form a spiro ring structure such as a 5-membered ring or a 6-membered ring by binding to each other via an intervening group such as —$(CH_2)_4$— or —$(CH_2)_5$—.

X is a hetero atom such as oxygen atom, nitrogen atom, and sulfur atom which may be substituted with a substituent.

The process of the present invention is useful in producing the optically active amine by starting from an imine represented by the general formula (b), and in particular, by starting from a condensed ring imine which is typically a benzylidene-N-substituted amine represented by the formula (b-1), a 1-(1,2,3,4-tetrahydronaphthylidene)-N-substituted amine represented by the formula (b-2), a N-substituted imino-3,4-dihydro-2H-1-benzopyrane represented by the formula (b-3), or an isoquinoline alkaloid derivative represented by the formula (b-4) to thereby produce the corresponding optically active amine represented by the following general formulae (c-1) to (c-4):

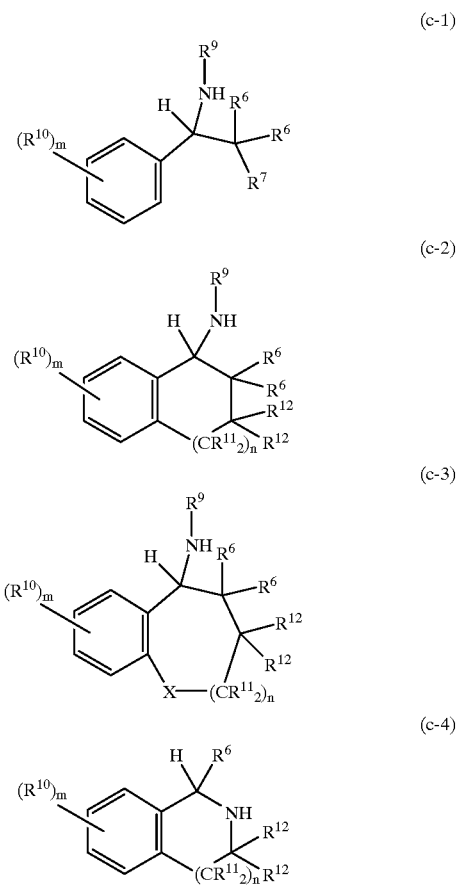

wherein $R^6$ to $R^{12}$, n and m are as defined above for the general formulae (b) or (b-1) to (b-4).

Exemplary optically active amines represented by (c-1) to (c-4) include N-methyl-1-phenethylamine, N-benzyl-1-phenethylamine, N-hydroxy-1-phenethylamine, N-methoxy-1-phenethylamine, N-benzyloxy-1-phenethylamine, N-benzoyloxy-1-phenethylamine, N-benzoylamino-1-phenethylamine, N-(1-phenethyl)-4-methylbenzenesulfonamide, N-(1-phenethyl) diphenylphosphonamide, N-(1-phenethyl) diethoxyphosphonamide, N-[1-(1,2,3,4-tetrahydronaphthyl) ethyl]diphenylphosphonamide, N-(1-cyclohexylethyl) diphenylphosphonamide, and 1,2,3,4-tetrahydroisoquinoline.

The optically active metal compound used as a catalyst in the process of the present invention is not particularly limited and exemplary optically active metal compounds include complexes of at least one transition metal selected from titanium, vanadium, manganese, iron, cobalt, zinc, nickel, ruthenium, rhodium, hafnium, and zirconium. Among these, the typical complexes of at least one transition metal selected from titanium, vanadium, manganese, iron, cobalt, nickel and ruthenium are optically active titanium (IV) complex, optically active iron (III) complex, optically active ruthenium (III) complex, optically active oxovanadium (IV) complex, optically active manganese (III) complex, optically active cobalt (II) complex, and optically active cobalt (III) complex.

In the process of the present invention, use of the optically active cobalt (II) complex represented by the following general formula (a):

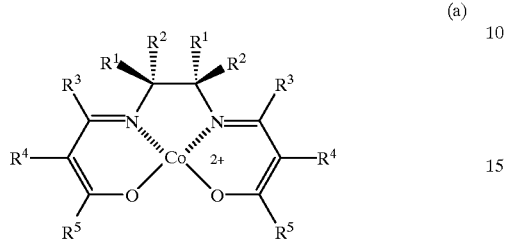

(a)

is preferred for producing the optically active amine at a high optical yield.

In the general formula (a) representing the optically active cobalt (II) complex, $R^1$ and $R^2$ are different from each other, and may be independently hydrogen atom, a straight chain or branched alkyl group, or an aryl group which may be optionally substituted with a substituent. Typical straight chain or branched alkyl groups include methyl group, ethyl group, isopropyl group, t-butyl group, sec-butyl group, n-propyl group, and n-butyl group, and typical aryl groups include phenyl group, p-methoxyphenyl group, p-chlorophenyl group, p-fluorophenyl group, α-naphthyl group, and β-naphthyl group.

$R^1$ and $R^1$ or $R^2$ and $R^2$ may together form a ring; and for example, $R^1$ and $R^1$ or $R^2$ and $R^2$ may form a 6-membered ring by binding to each other via an intervening group such as —$(CH_2)_4$—.

$R^3$, $R^4$ and $R^5$ may be the same or different from each other, and are independently hydrogen atom, a straight chain or branched alkyl group, an aryl group, an acyl group, or an alkoxycarbonyl group which may be optionally substituted with a substituent; and $R^4$, $R^5$, and the carbon atoms having $R^4$ and $R^5$ bonded thereto may together form a ring. Typical straight chain or branched alkyl groups include methyl group, ethyl group, isopropyl group, t-butyl group, sec-butyl group, n-propyl group, and n-butyl group, and typical aryl groups include phenyl group, p-methoxyphenyl group, p-chlorophenyl group, p-fluorophenyl group, and naphthyl group. Typical acyl groups include acetyl group, perfluoroacetyl group, propionyl group, butylyl group, isobutylyl group, and pivaloyl group, and typical alkoxycarbonyl groups include methoxycarbonyl group, cyclopentyloxycarbonyl group, cyclohexyloxycarbonyl group, cyclooctyloxycarbonyl group, and benzyloxycarbonyl group. When $R^4$ and $R^5$ together represent —CH=CH—CH=CH— by bonding to each other, a benzene ring is formed, and this benzene ring may be substituted with an alkyl group such as methyl group, ethyl group, isopropyl group, or t-butyl group, or an aryl group such as phenyl group or naphthyl group, and alternatively, this benzene ring may form a condensed ring such as naphthalene ring through condensation.

Exemplary optically active cobalt (II) complexes represented by the general formula (a) include those represented by the following formulae (a-1) to (a-17):

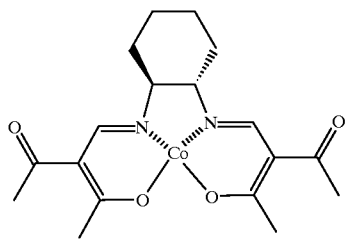

(a-1)

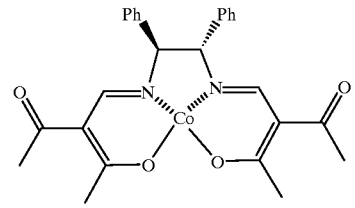

(a-2)

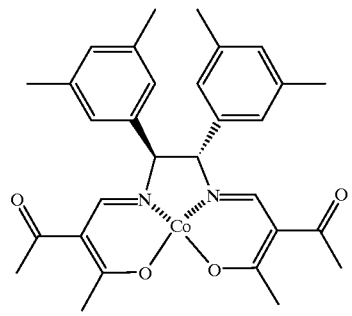

(a-3)

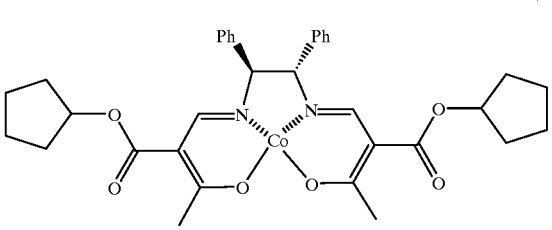

(a-4)

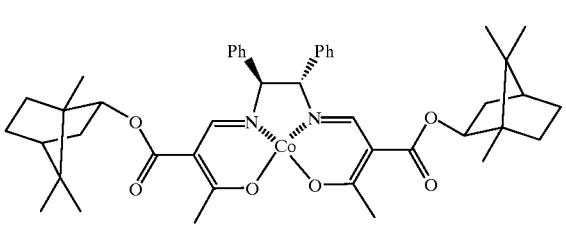

(a-5)

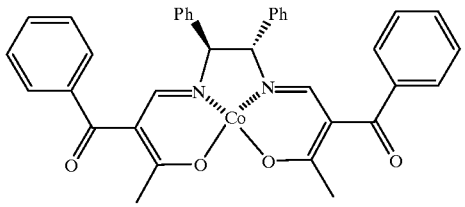

(a-6)

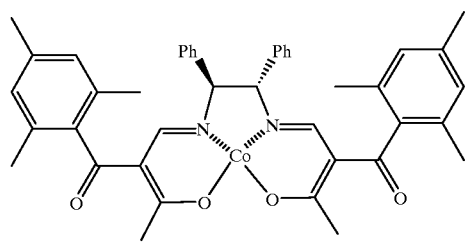
(a-7)
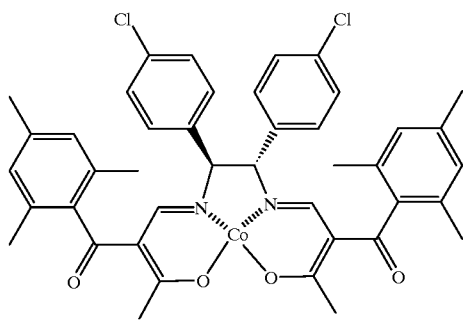
(a-8)
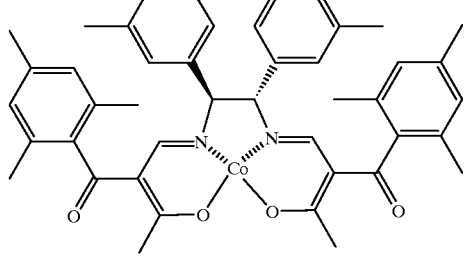
(a-9)
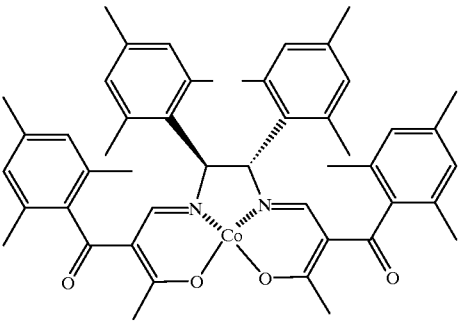
(a-10)
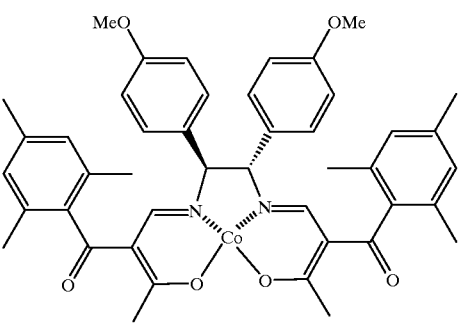
(a-11)
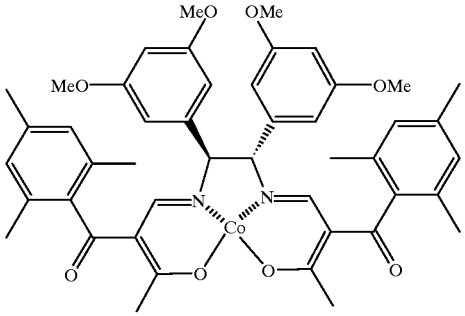
(a-12)
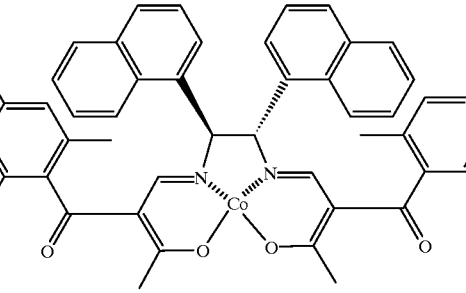
(a-13)
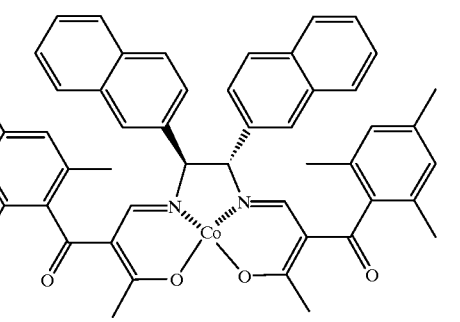
(a-14)
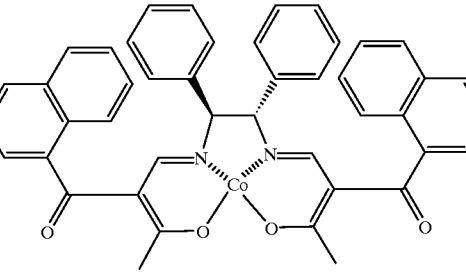
(a-15)
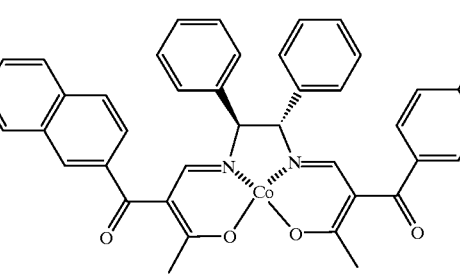
(a-16)

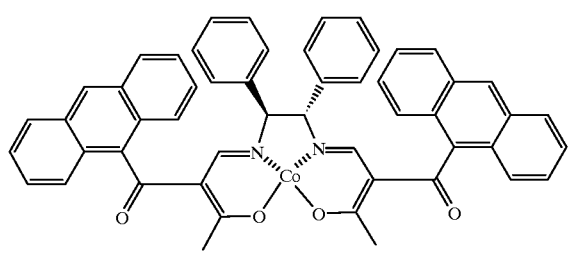

(a-17)

The optically active cobalt (II) complexes represented by the general formula (a) may be prepared in accordance with the known method such as Y. Nlshida et al., Inorg. Chim. Acta, 38, 213 (1980); L. Claisen, Ann. Chem., 297, 57 (1987); and E. G. Jager, Z. Chem., 8, 30, 392 and 475 (1968). For example, the optically active cobalt (II) complex may be prepared by formylating a 1,3-diketone derivative, dehydrating and condensing the formylated 1,3-diketone with 1,2-diphenyldiamine derivative (optically active diamine) which is the asymmetry source to thereby form the ligand, adding aqueous solution of cobalt (II) chloride in the presence of sodium hydroxide, and heating the mixture. For example, the optically active cobalt (II) complex represented by the formula (a-7) may be prepared by the steps shown below in (e-1) and (e-2).

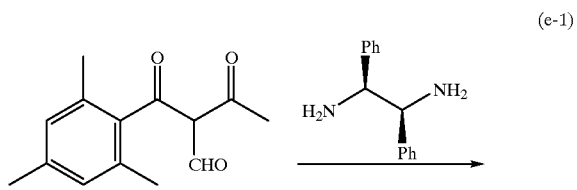

(e-1)

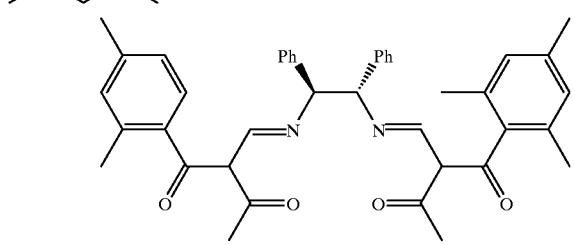

(e-2)

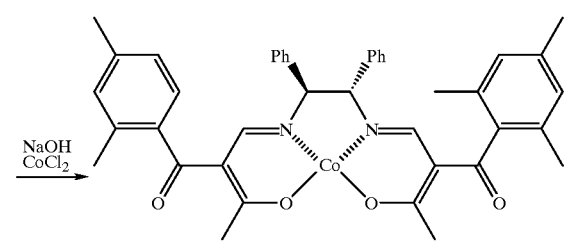

In the production of the optically active cobalt (II) complex, formylation of the 1,3-diketone may be accomplished, for example, by adding 1 to 5 mole equivalents of trimethyl orthoformate, and heating the mixture under reflux in acetic anhydride solvent.

The dehydration and condensation reaction with the optically active diamine is accomplished by adding 2 equivalents of the formylated 1,3-diketone to the optically active amine in an alcoholic solvent, stirring the mixture at room temperature for 1 to 2 hours, and heating the mixture to 50° C. The crude product obtained by concentration may be purified by any of the conventional process such as silica gel column chromatography, reprecipitation, and recrystallization.

In the complex formation reaction between the ligand and the cobalt dichloride, the sodium hydroxide is used in an amount of at least 2.0 mole equivalents, and preferably in an amount of 2.0 to 3.0 mole equivalents in relation to the ligand.

In addition, the aqueous solution of cobalt (II) chloride is used such that the amount of cobalt (II) chloride is at least 1.0 mole equivalents, and preferably 1.0 to 1.5 mole equivalents in relation to the ligand.

The reaction is effected in nitrogen or argon gas stream, and the solvent and the water added is preliminarily degassed. The reaction can be accomplished when the reaction temperature is at least 0° C. The reaction, however, can be completed in a shorter reaction period when the reaction mixture is heated to about 30 to 80° C., and more preferably, to 40 to 60° C.

The solvent used is preferably an alcoholic solvent such as methanol, ethanol or 2-propanol, or a halogenated hydrocarbon solvent such as dichloromethane or chloroform, although the type of the solvent used is not particularly limited. Other solvents such as acetone, acetonitrile, N,N-dimethylformamide, and tetrahydrofuran may also be used.

In the production of the optically active cobalt (II) complex, precipitation of the optically active cobalt (II) complex starts immediately (i.e. in 1 to 10 minutes) after the addition of the aqueous solution of cobalt (II) chloride, and the heating and stirring is continued for further 30 minutes to 2 hours. The reaction mixture is then cooled to room temperature and, if desired, water is added to fully precipitate the reaction product. The precipitate is separated by filtration and washed with water in nitrogen atmosphere, and dried under vacuum to obtain the target product.

The optically active cobalt (II) complex produced in the present invention is easily oxidized by the dissolved oxygen in the solvent, and therefore, the optically active cobalt (II) complex may be preliminarily doped with iodine before its structural analysis for conversion into optically active cobalt (III) complex which is stable in air and convenient to handle. More illustratively, 0.5 mole equivalent of iodine ($I_2$) is added to the optically active cobalt (II) complex in the solvent of dichloromethane, and the mixture is stirred at room temperature for reaction. The product obtained by concentration is then recrystallized from dichloromethane-diethyl ether-hexane to obtain crystalline cobalt (III) complex which is adapted for X-ray analysis to thereby conduct the analysis. For example, the optically active cobalt (II) complex represented by the formula (a-10) may be iodized by the process as described above for conversion into the optically active cobalt (III) complex represented by the following formula (a-18) to enable the structural analysis by X-ray diffraction. The optically active cobalt (III) complex represented by the formula (a-18) is also effective as a catalyst used in the process of the present invention.

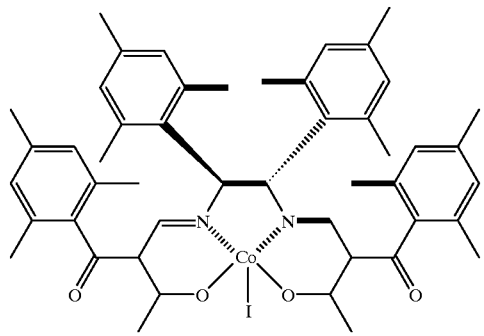

(a-18)

When the optically active cobalt (II) complex represented by the general formula (a) is used for the catalyst in the process of the present invention, 0.001 to 50% by mole of such complex is reacted with 1 mole of the imine, preferably 0.01 to 50% by mole and more preferably, 0.05 to 10% by mole of such complex is reacted with 1 mole of the imine to thereby obtain the optically active amine at a high optical yield and at a high chemical yield.

In the process of the present invention, an imine is reacted with a hydride reagent by using an optically active metal compound which is typically the optically active cobalt (II) complex represented by the general formula (a) for the catalyst, and the reaction is preferably conducted in the presence of an alcohol compound and/or a carboxylic acid compound.

A typical alcohol compounds used is the compound represented by the following formula (d):

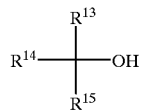

(d)

In formula (d) $R^{13}$, $R^{14}$ and $R^{15}$ may be the same or different, and may be hydrogen atom, a straight chain or branched alkyl group, a cycloalkyl group, an aryl group, or a straight chain or branched ether group containing a hetero atom which may be optionally substituted with a substituent such as hydroxyl group, amino group, ester group, or carbonyl group. Exemplary straight chain or branched alkyl groups in the formula (d) include methyl group, ethyl group, n-propyl group, isopropyl group, t-butyl group, sec-butyl group, and n-butyl group. Exemplary cycloalkyl groups include cyclopentyl group, cyclohexyl group, and cycloheptyl group. Exemplary aryl groups include, phenyl group, p-methoxyphenyl group, p-chlorophenyl group, p-fluorophenyl group, and naphthyl group. Exemplary straight chain or branched ether groups containing a hetero atom include methoxyethyl group, methoxypropyl group, 2-furyl group, 3-furyl group, and 2-tetrahydropyranyl group. $R^{14}$ and $R^{15}$ may together form a ring, and, for example, $R^{14}$ and $R^{15}$ may form a 5-membered ring or a 6-membered ring by binding to each other via an intervening group such as —(CH$_2$)$_4$— or —(CH$_2$)$_5$—.

Examples of the alcohol compound include aliphatic and alicyclic alcohols such as methanol, ethanol, 2,2,2-trifluoroethanol, propanol, isopropanol, butanol, sec-butanol, t-butanol, cyclopentanol, cyclohexanol, and cyclo- heptanol; aromatic alcohols such as phenol, resorcinol and 2-hydroxypyridine; polyalcohols such as ethylene glycol and propylene glycol; acyclic and cyclic ether alcohols such as ethylene glycol monomethyl ether, ethylene glycol monoethyl ether, propylene glycol monomethyl ether, tetrahydrofurfuryl alcohol, tetrahydropyrane-2-methanol, furfuryl alcohol, tetrahydro-3-furan-methanol, 2,2-dimethyl-1,3-dioxolan-4-methanol; lactone alcohols such as dihydro-5-(hydroxymethyl)-2(3H)-furanone; and acyclic and cyclic amino alcohols such as 2-(methylamino) ethanol, 2-(ethylamino) ethanol, 2-pyridine methanol, 2-pyperidine methanol, 1-methyl-2-pyperidine methanol, 1-methyl-2-pyrrolidine methanol. Among these, use of an aliphatic alcohol is preferred for producing the optically active amine at a high optical yield and at a high chemical yield.

In the process of the present invention, the alcohol compound represented by the general formula (d) may be used either alone or in combination of two or more compounds. Exemplary typical combinations of two or more such compounds include ethanol/ethylene glycol, ethanol/propylene glycol, ethanol/ethylene glycol monomethyl ether, ethanol/propylene glycol monomethyl ether, ethanol/tetrahydrofurfuryl alcohol, ethanol/tetrahydropyrane-2-methanol, ethanol/furfuryl alcohol, ethanol/tetrahydro-3-furan-methanol, and ethanol/5-methyltetrahydrofuran-2-methanol, and the combinations wherein methanol, propanol, butanol, 2-propanol, 2,2-dimethyl ethanol, 2,2,2-trifluoroethanol, cyclopentanol, or cyclohexanol is used instead of the ethanol in the above-mentioned combinations.

Typical carboxylic acid compound which is used alone or in combination with the alcohol compound is the compound represented by the following formula (f):

(f)

In formula (f), $R^{16}$ is hydrogen atom, or a straight chain or branched alkyl group, a cycloalkyl group, an aryl group, or a straight chain or branched ether group containing a hetero atom which may be optionally substituted with a substituent such as hydroxyl group, amino group, ester group, or carbonyl group. Exemplary straight chain or branched alkyl groups of $R^{16}$ include methyl group, ethyl group, n-propyl group, isopropyl group, t-butyl group, sec-butyl group, n-butyl group, trifuluoromethyl group, and 2,2,2-trifluoroethyl group. Exemplary cycloalkyl groups include cyclopentyl group, cyclohexyl group, and cycloheptyl group. Exemplary aryl groups include, phenyl group, p-methoxyphenyl group, p-chlorophenyl group, p-fluorophenyl group, and naphthyl group. Exemplary straight chain or branched ether groups containing a hetero atom include methoxyethyl group, methoxypropyl group, 2-furyl group, 3-furyl group, and 2-tetrahydropyranyl group.

Exemplary carboxylic acid compounds include aliphatic or alicyclic carboxylic acids and dicarboxylic acids such as formic acid, acetic acid, propionic acid, isobutanoic acid, trifluoroacetic acid, pentafluoroethanecarboxylic acid, and malonic acid; aromatic carboxylic acids and dicarboxylic acids such as benzoic acid, phenylacetic acid, 3,3,3-triphenylacetic acid, methoxyphenyl acetic acid, pyran-2-carboxylic acids, and 2-thiophenecarboxylic acids; acyclic or cyclic carboxylic acids and dicarboxylic acids such as methoxyacetic acid. Among these, use of an aliphatic or aryl carboxylic acids is preferred for producing the optically active amine at a high optical yield and at a high chemical yield.

In the process of the present invention, the carboxylic acid compound may be used either alone or in combination of two or more compounds.

When the alcohol compound and/or the carboxylic acid compound is used in the process of the present invention, 0.01 to 50 moles of such compounds in total is reacted with 1 mole of the imine, and more preferably, 1 to 30 moles of such compounds is reacted with 1 mole of the imine to thereby obtain the optically active amine at a high optical yield and at a high chemical yield.

The metal hydrides which may be used as the hydride reagent in the process of the present invention are not limited, and typical metal hydrides include lithium aluminum hydride, lithium aluminum tri(t-butoxy)hydride, lithium borohydride, sodium borohydride, potassium borohydride, calcium borohydride, ammonium borohydride, and sodium cyanoborohydride.

The hydride reagent used in the present invention may also be the one which undergoes a metal exchange when used with a metal chloride such as titanium chloride, rubidium chloride, or cerium chloride, or a quaternary ammonium salt such as tetramethylammonium chloride or tetrabutylammonium bromide.

When a trialkoxy metal hydride complex compound such as sodium tri(methoxy)borohydride, sodium tri(ethoxy) borohydride, sodium tri(isopropoxy)borohydride, sodium tri(t-butoxy)borohydride, potassium tri(isopropoxy) borohydride, or potassium tri(t-butoxy)borohydride is used, the optically active amine can be produced at a high optical yield and at a high chemical yield without using the alcohol compound represented by the general formula (d).

When a tri(carboxylic acid)metal hydride complex compound such as sodium tri(acetic acid)borohydride, sodium tri(ethylcarboxylic acid)borohydride, or sodium tri (fluoroacetic acid)borohydride is used, the optically active amine can be produced at a high optical yield and at a high chemical yield without using the carboxylic acid compound represented by the general formula (f).

In the process of the present invention, the reaction as described above is preferably allowed to take place in liquid phase, and a solvent may be used in the reaction as desired. Exemplary useful solvents include aliphatic hydrocarbon solvents, aromatic hydrocarbon solvents, alicyclic hydrocarbon solvents, ester solvents, ether solvents, and halogen solvents. Among these, the preferred are halogen solvents such as carbon tetrachloride, chloroform, and flon 113; aromatic hydrocarbon solvents such as toluene, and ether solvents such as ethylene glycol dimethyl ether and tetrahydrofuran.

When the solvent is used, the solvent is generally used in an amount of about 1 ml to 1 liter per 1 mmol of the imine, and the use in an amount of about 5 to 100 ml per 1 mmol of the imine is effective for obtaining the optically active amine at a high optical yield and at a high chemical yield.

The reaction is generally conducted at a reaction temperature preferably in the range of −100 to 50° C., more preferably in the range of −80 to 30° C., and most preferably in the range of −60 to 25° C. The reaction pressure may be normal pressure as long as the solvent is not vaporized.

The reaction period is generally from about 1 minutes to 10 days. The reaction progress may be checked by collecting a sample from the reaction mixture and analyzing the sample by thin layer chromatography (TLC), gas chromatography (GC), or the like as occasion demands.

In the process of the present invention, the optically active amine of interest may be recovered and purified from the reaction mixture by an adequate combination of conventional procedures such as distillation, adsorption, extraction, recrystallization, and the like.

EXAMPLES

Next, the present invention is described in further detail by referring to Examples which by no means limit the scope of the present invention.

(Example 1)

To a reaction vessel charged with 0.75 mmol of sodium borohydride was added 2.0 ml of chloroform, and then, 0.25 ml of ethanol in argon atmosphere, and the mixture was stirred at room temperature for 30 minutes. The reaction mixture was cooled to −20° C., and 1.5 ml chloroform solution of 0.025 mmol optically active cobalt (II) complex represented by the formula (a-7) was added dropwise to the mixture. After stirring at −20° C. for 15 minutes, 1.5 ml chloroform solution of 0.5 mmol P,P-diphenyl-N-[1-(1,2,3, 4-tetrahydronaphthylidene)]phosphonamide was slowly added dropwise. Stirring of the mixture was kept at −20° C., and the reaction was completed in 5 days. The resulting reaction compound was separated from the reaction mixture for purification by silica gel chromatography to quantitatively obtain optically active N-[1-(1,2,3,4-tetrahydronaphthyl)ethyl]diphenylphosphonamide. The optical purity of the resulting compound analyzed by high performance liquid chromatography (optically active column, manufactured by DAICEL CHEMICAL INDUSTRIES, LTD, CHIRALPAK AD) was 85% e.e.

(Example 2)

To a reaction vessel charged with 0.75 mmol of sodium borohydride was added 5.0 ml of chloroform, and then, 1 ml of ethanol and 1 ml of tetrahydrofurfuryl alcohol in argon atmosphere, and the mixture was stirred at room temperature for 30 minutes. The reaction mixture was cooled to −20° C., and 2 ml chloroform solution of 0.025 mmol optically active cobalt (II) complex represented by the formula (a-7) was added dropwise to the solution. After stirring at −20° C. for 15 minutes, 2 ml chloroform solution of 0.5 mmol P,P-diphenyl-N-[1-(1,2,3,4-tetrahydronaphthylidene)] phosphonamide was slowly added dropwise. Stirring of the mixture was kept at −20° C., and the reaction was completed in one day. The resulting reaction compound was separated from the reaction mixture for purification by silica gel chromatography to quantitatively obtain optically active N-[1-(1,2,3,4-tetrahydronaphthyl)ethyl] diphenylphosphonamide. The optical purity of the resulting compound analyzed by high performance liquid chromatography (optically active column, manufactured by DAICEL CHEMICAL INDUSTRIES LTD, CHIRALPAK AD) was 92% e.e.

(Example 3)

To first reaction vessel was added 5.0 ml chloroform suspension of 0.75 mmol of sodium borohydride, and then, 0.75 ml of ethanol and 1 ml of tetrahydrofurfuryl alcohol in argon atmosphere, and the mixture was stirred at 0° C. for 3 hours. Next, to second reaction vessel were added 2.0 ml chloroform solution of 0.005 mmol optically active cobalt (II) complex represented by the formula (a-7), 0.75 mmol of ethanol, and 2.0 ml chloroform solution of 0.5 mmol P,P-diphenyl-N-[1-(1,2,3,4-tetrahydronaphthylidene)] phosphonamide in argon atmosphere, and the mixture was stirred with the mixture being cooled to −20° C. The reaction mixture prepared in the first reaction vessel was slowly added dropwise to the second reaction vessel, and the mixture was stirred at −20° C. The reaction ceased in 2 hours. After the conventional post treatments, the resulting reaction mixture was separated for purification by silica gel chromatography to quantitatively obtain optically active N-[1-(1,2,3,4-tetrahydronaphthyl)ethyl] diphenylphosphonamide. The optical purity of the resulting compound analyzed by high performance liquid chromatography (optically active column, manufactured by DAICEL CHEMICAL INDUSTRIES LTD, CHIRALPAK AD) was 92% e.e.

(Example 4)

To first reaction vessel was added 5.0 ml chloroform suspension of 0.75 mmol of sodium borohydride, and then, 0.75 ml of ethanol and 1 ml of tetrahydrofurfuryl alcohol in argon atmosphere, and the mixture was stirred at 0° C. for 3 hours. Next, to second reaction vessel were added 2.0 ml chloroform solution of 0.005 mmol optically active cobalt (II) complex represented by the formula (a-7), 0.75 mmol of ethanol, and 2.0 ml chloroform solution of 0.5 mmol P,P-diphenyl-N-[1-(1,2,3,4 -tetrahydronaphthylidene)] phosphonamide in argon atmosphere, and the mixture was stirred with the mixture being cooled to 0° C. The reaction mixture prepared in the first reaction vessel was slowly added dropwise to the second reaction vessel, and the mixture was stirred at 0° C. The reaction ceased in 80 minutes. After the conventional post treatments, the resulting reaction mixture was separated for purification by silica gel chromatography to quantitatively obtain optically active N-[1-(1,2,3,4-tetrahydronaphthyl)ethyl] diphenylphosphonamide. The optical purity of the resulting compound analyzed by high performance liquid chromatography (optically active column, manufactured by DAICEL CHEMICAL INDUSTRIES LTD, CHIRALPAK AD) was 92% e.e.

(Example 5)

The procedure of Example 4 was repeated except that methanol was used instead of the ethanol. The reaction was completed in 80 minutes, and N-[1-(1,2,3,4-tetrahydronaphthyl)ethyl]diphenylphosphonamide was quantitatively obtained. The resulting product had an optical purity of 92% e.e.

(Example 6)

The procedure of Example 4 was repeated except that P,P-diphenyl-N-(α-methylbenzylidene)phosphonamide was used instead of the P,P-diphenyl-N-[1-(1,2,3,4-tetrahydronaphthylidene)]phosphonamide, and the compound represented by the formula (a-10) was used for the optically active cobalt (II) complex. The reaction was completed in 80 minutes, and N-(1-phenetyl) diphenylsulfonamide was quantitatively obtained. The resulting product had an optical purity of 90% e.e.

(Example 7)

The procedure of Example 4 was repeated except that acetic acid was used instead of the ethanol. Conversion of the reaction after one day was 10%. The resulting product had an optical purity of 12% e.e.

(Example 8)

The procedure of Example 4 was repeated except that 4-methyl-N-[1-(1,2,3,4-tetrahydronaphthylidene)] benzenesulfonamide was used instead of the P,P-diphenyl-N-[1-(1,2,3,4-tetrahydronaphthylidene)]phosphonamide. The reaction was completed in 30 minutes, and N-[1-(1,2,3,4-tetrahydronaphthyl)ethyl]-4-methylbenzenesulfonamide was quantitatively obtained. The resulting product had an optical purity of 65% e.e.

(Example 9)

The procedure of Example 4 was repeated except that N-(α-methylbenzilidene)benzylamine was used instead of the P,P-diphenyl-N-[1-(1,2,3,4-tetrahydronaphthylidene)] phosphonamide. The reaction was completed in 10 minutes, and α-tetralone-N-benzylamine was quantitatively obtained. The resulting product had an optical purity of 15% e.e.

(Example 10)

The procedure of Example 4 was repeated except that 1-methyl-6,7-dimethoxy-3,4-dihydroisoquinoline was used instead of the P,P-diphenyl-N-[1-(1,2,3,4-tetrahydronaphthylidene)]phosphonamide. The reaction was completed in 10 minutes, and an optically active amine was quantitatively obtained. The resulting product had an optical purity of 5% e.e.

(Example 11)

The procedure of Example 4 was repeated except that 1-methyl-6,7-dimethoxy-3,4-dihydroisoquinoline was used instead of the P,P-diphenyl-N-[1-(1,2,3,4-tetrahydronaphthylidene)]phosphonamide, and acetic acid was used instead of the ethanol. The reaction was completed in 10 minutes, and an optically active amine was quantitatively obtained. The resulting product had an optical purity of 25% e.e.

(Example 12)

The procedure of Example 4 was repeated except that 1-methyl-6,7-dimethoxy-3,4-dihydroisoquinoline was used instead of the P,P-diphenyl-N-[1-(1,2,3,4-tetrahydronaphthylidene)]phosphonamide, tetramethylammonium borohydride was used instead of the sodium borohydride, and acetic acid was used instead of the ethanol. The reaction was completed in 20 minutes, and an optically active amine was quantitatively obtained. The resulting product had an optical purity of 30% e.e.

(Example 13)

The procedure of Example 4 was repeated except that 1-methyl-6,7-dimethoxy-3,4-dihydroisoquinoline was used instead of the P,P-diphenyl-N-[1-(1,2,3,4-tetrahydronaphthylidene)]phosphonamide, tetramethylammonium borohydride was used instead of the sodium borohydride, acetic acid was used instead of the ethanol, and triethoxyborane was further added. The reaction was completed in 20 minutes, and an optically active amine was quantitatively obtained. The resulting product had an optical purity of 30% e.e.

(Examples 14 to 19)

The procedure of Example 4 was repeated except that the imine shown in Table 1 was used instead of the P,P-diphenyl-N-[1-(1,2,3,4-tetrahydronaphthylidene)] phosphonamide, and the complex represented by the formula (a-9) was used for the optically active cobalt (II) complex. The reaction was completed in 12 hours, and an optically active amine was quantitatively obtained in each of the examples. The optical purity of the resulting products analyzed are also shown in Table 1.

TABLE 1-1

| Example | Imine compound | Chemical yield (%) | Optical purity (% e.e.) |
|---|---|---|---|
| 14 | (indanone N-diphenylphosphinyl imine) | quant. | 91 |
| 15 | (indanone N-diphenylphosphinyl imine) | quant. | 98 |
| 16 | (benzosuberone N-diphenylphosphinyl imine) | quant. | 94 |
| 17 | (chromanone N-diphenylphosphinyl imine) | quant. | 92 |
| 18 | (chromanone N-diphenylphosphinyl imine) | quant. | 80 |
| 19 | (phenyl propyl ketone N-diphenylphosphinyl imine) | quant. | 74 |

TABLE 1-2

| Example | Imine compound | Chemical yield (%) | Optical purity (% e.e.) |
|---|---|---|---|
| 20 | (phenylacetylene methyl ketone N-diphenylphosphinyl imine) | 79 | 62 |
| 21 | (cyclohexyl methyl ketone N-diphenylphosphinyl imine) | 87 | 63 |

(Example 22)

5 mmol of methanol/HCl reagent was added to 5 ml methanol solution of 0.5 mmol α-tetralone N-diphenylphosphinylamine obtained in Example 15 under nitrogen atmosphere, and the mixture was stirred at room temperature for 3 hours for reaction. After the conventional post treatments, the resulting reaction mixture was separated for purification by silica gel chromatography to obtain optically active 1,2,3,4-tetrahydro-1-naphthylamine at an yield of 87%. The product had an optical purity of 98% e.e.

(Example 23)

The procedure of Example 8 was repeated except that the optically active cobalt (II) complex represented by the formula (a-19) of Table 2 was used instead of the optically active cobalt (II) complex represented by the formula (a-7). The reaction was completed in 6 hours, and N-[1-(1,2,3,4-tetrahydronaphthyl)ethyl]-4-methylbenzenesulfonamide shown in Table 2 was quantitatively obtained. The resulting product had an optical purity of 48% e. e. The results are shown in Table 2.

(Example 24)

The procedure of Example 21 was repeated except that the optically active titanium (IV) complex represented by the formula (g-1) of Table 2 was used instead of the optically active cobalt (II) complex represented by the formula (a-19). The reaction was completed in 6 hours, and N-[1-(1,2,3,4-tetrahydronaphthyl)ethyl]-4-methylbenzenesulfonamide shown in Table 2 was quantitatively obtained. The resulting product had an optical purity of 11% e. e. The results are shown in Table 2.

(Example 25)

The procedure of Example 21 was repeated except that the optically active ruthenium (IV) complex represented by the formula (h-1) of Table 2 was used instead of the optically active cobalt (II) complex represented by the formula (a-19). The reaction was completed in 6 hours, and N-[1-(1,2,3,4- tetrahydronaphthyl)ethyl]-4-methylbenzenesulfonamide shown in Table 2 was quantitatively obtained. The resulting product had an optical purity of 6% e.e. The results are shown in Table 2.

TABLE 2

| Example | Complex catalyst | Chemical yield (%) | Optical purity (% e.e.) |
|---|---|---|---|
| 23 | 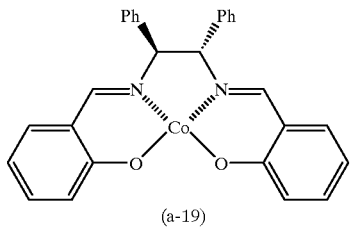 (a-19) | quant. | 48% ee |
| 24 | 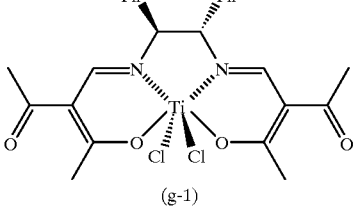 (g-1) | quant. | 11% ee |
| 25 | 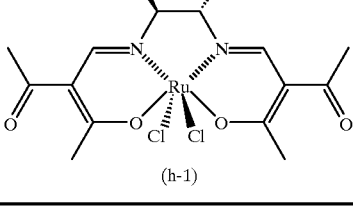 (h-1) | quant. | 6% ee |

INDUSTRIAL UTILITY

The process of the present invention is capable of producing an optically active amine from an imine by using sodium borohydride and the like which are safe as well as inexpensive for the hydride agent. The thus produced optically active amine is useful as an intermediate in synthesizing physiologically active compounds such as pharmaceuticals and agricultural chemicals, as a functional material such as a liquid crystal, and as a starting material in synthesizing fine chemicals.

What is claimed is:

1. A process for producing an optically active amine, comprising the step of:
   reacting an imine with a hydride reagent in the presence of an optically active metal compound,
   wherein said hydride reagent is a metal hydride, a reagent that undergoes a metal exchange, a metal trialkoxy hydride complex compound or a metal tri(carboxylic acid) hydride complex compound,
   wherein said optically active metal compound is a transition-metal complex, and
   wherein said optically active metal complex is used in an amount of from about 0.01 to 50% by mole per mole of the imine; and
   carrying out said reaction in an inert atmosphere.

2. A process for producing an optically active amine, comprising the step of:
   reacting an imine with a hydride reagent in the presence of an optically active metal compound and an alcohol compound, wherein said hydride reagent is a metal hydride, a reagent that undergoes a metal exchange, a metal trialkoxy hydride complex compound or a metal tri(carboxylic acid) hydride complex compound,
   wherein said optically active metal compound is a transition-metal complex, and
   wherein said optically active metal complex is used in an amount of from about 0.01 to 50% by mole per mole of the imine; and
   carrying out said reaction in an inert atmosphere.

3. A process for producing an optically active amine, comprising the step of:
   reacting an imine with a hydride reagent in the presence of an optically active metal compound and a carboxylic acid compound,
   wherein said hydride reagent is a metal hydride, a reagent that undergoes a metal exchange, a metal trialkoxy hydride complex compound or a metal tri(carboxylic acid) hydride complex compound,
   wherein said optically active metal compound is a transition-metal complex, and
   wherein said optically active metal complex is used in an amount of from about 0.01 to 50% by mole per mole of the imine; and
   carrying out said reaction in an inert atmosphere.

4. A process for producing an optically active amine, comprising the step of: reacting an imine with a hydride reagent in the presence of an optically active metal compound, an alcohol compound and a carboxylic acid compound, wherein said hydride reagent is a metal hydride, a reagent that undergoes a metal exchange, a metal trialkoxy hydride complex compound or a metal tri(carboxylic acid) hydride complex compound, wherein said optically active metal compound is a transition-metal complex, and wherein said optically active metal complex is used in an amount of from about 0.01 to 50% by mole per mole of the imine; and carrying out said reaction in an inert atmosphere.

5. A process for producing an optically active amine according to any one of claims 1 to 4 wherein said optically active metal compound is an optically active cobalt (II) complex.

6. A process for producing an optically active amine according to any one of claims 1 to 4 wherein said optically active metal compound is an optically active cobalt (III) complex.

7. A process for producing an optically active amine according to claim 5 wherein said optically active cobalt (II) complex is a compound represented by the following general formula (a):

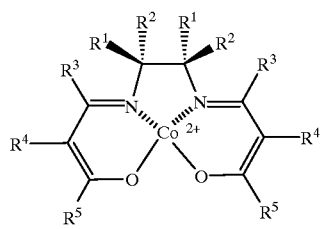

(a)

wherein $R^1$ and $R^2$ are different from each other, and are independently hydrogen atom, a straight chain or branched alkyl group or an aryl group which may be optionally substituted with a substituent; and $R^1$ and $R^1$ or $R^2$ and $R^2$ may together form a ring; and $R^3$, $R^4$ and $R^5$ are the same or different from each other, and are independently hydrogen atom, a straight chain or branched alkyl group, an aryl group, an acyl group, or an alkoxycarbonyl group which may be optionally substituted with a substituent; and $R^4$, $R^5$, and the carbon atoms having $R^4$ and $R^5$ bonded thereto may together form a ring.

8. A process for producing an optically active amine according to any one of claims 1 to 4 wherein said hydride reagent is a metal hydride.

9. A process for producing an optically active amine according to claim 2 or 4 wherein one alcohol compound or a combination of two or more alcohol compounds is used for said alcohol compound.

10. A process for producing an optically active amine according to claim 3 or 4 wherein one carboxylic acid compound or a combination of two or more carboxylic acid compounds is used for said carboxylic acid compound.

11. A process for producing an optically active amine according to claim 4 wherein one alcohol compound or a combination of two or more alcohol compounds is used for said alcohol compound; and one carboxylic acid compound or a combination of two or more carboxylic acid compounds is used for said carboxylic acid compound.

* * * * *